United States Patent
Oguri et al.

(10) Patent No.: US 9,835,639 B2
(45) Date of Patent: Dec. 5, 2017

(54) GRIPPING MECHANISM

(71) Applicants: FUJIREBIO INC., Tokyo (JP); JEOL LTD., Tokyo (JP)

(72) Inventors: Kazuyuki Oguri, Tokyo (JP); Tomohiro Endo, Tokyo (JP); Toshiaki Ohtake, Tokyo (JP); Hidenobu Kawada, Tokyo (JP); Takahiro Matsumoto, Tokyo (JP)

(73) Assignees: FUJIREBIO INC., Tokyo (JP); JEOL LTD., Tokyo (JP)

( * ) Notice: Subject to any disclaimer, the term of this patent is extended or adjusted under 35 U.S.C. 154(b) by 0 days.

(21) Appl. No.: 14/952,436

(22) Filed: Nov. 25, 2015

(65) Prior Publication Data

US 2016/0154017 A1    Jun. 2, 2016

Related U.S. Application Data

(63) Continuation-in-part of application No. PCT/JP2014/063904, filed on May 27, 2014.

(30) Foreign Application Priority Data

May 30, 2013   (JP) ................................ 2013-114649

(51) Int. Cl.
*B65G 17/20* (2006.01)
*G01N 35/00* (2006.01)
(Continued)

(52) U.S. Cl.
CPC ...... *G01N 35/0099* (2013.01); *B25J 15/0028* (2013.01); *B25J 15/08* (2013.01);
(Continued)

(58) Field of Classification Search
CPC .... G01N 35/099; G01N 35/025; G01N 35/04; G01N 35/10; B25J 15/0028; B25J 15/08;
(Continued)

(56) References Cited

U.S. PATENT DOCUMENTS 3,012,811 A * 12/1961 Sandrock ............... G21C 19/10
                                                        294/110.1
3,648,427 A *  3/1972 Raudat ................... B65B 21/18
                                                        53/247
(Continued)

FOREIGN PATENT DOCUMENTS

DE   102010019348 A1   11/2011
EP      2514611 A1     10/2012
(Continued)

OTHER PUBLICATIONS

Chinese Application No. 201480031375.2; Office Action; 19 pages; dated Dec. 1, 2016.
(Continued)

*Primary Examiner* — William R Harp
(74) *Attorney, Agent, or Firm* — Shay Glenn LLP

(57) ABSTRACT

The gripping mechanism is a gripping mechanism for gripping a cuvette T, the gripping mechanism comprising: a sandwiching section 50 for holding the cuvette T in a laterally sandwiching manner; a pressing section 60 for pressing downward an upper end surface of the cuvette T held in a sandwiching manner by the sandwiching section 50, wherein the pressing section 60 is arranged such that, with the cuvette T being held in a sandwiching manner by the sandwiching section 50, a central axis of the cuvette T along a vertical direction coincides mutually with a central axis of the pressing section 60 in the vertical direction.

4 Claims, 10 Drawing Sheets

(51) Int. Cl.
*G01N 35/02* (2006.01)
*B25J 15/00* (2006.01)
*B25J 15/08* (2006.01)
*B25J 15/10* (2006.01)
*G01N 33/53* (2006.01)
*G01N 35/04* (2006.01)
*G01N 35/10* (2006.01)

(52) U.S. Cl.
CPC ............ *B25J 15/103* (2013.01); *B65G 17/20* (2013.01); *G01N 33/5302* (2013.01); *G01N 35/025* (2013.01); *G01N 35/04* (2013.01); *G01N 35/10* (2013.01); *G01N 2035/0465* (2013.01)

(58) Field of Classification Search
CPC ..... B25J 15/086; B25J 15/103; B65G 47/842; B65G 47/847
USPC ......... 198/678.1, 803.3, 803.7, 803.9, 803.8, 198/468.2, 750.11, 470.1; 294/115
See application file for complete search history.

(56) References Cited

U.S. PATENT DOCUMENTS

| | | | | |
|---|---|---|---|---|
| 4,034,542 | A * | 7/1977 | Loehr | A01D 46/247 294/111 |
| 4,036,353 | A * | 7/1977 | Suter | B65H 67/02 198/468.2 |
| 5,455,006 | A * | 10/1995 | Aota | G01N 35/04 422/561 |
| 5,693,113 | A * | 12/1997 | Dries | C03B 35/04 294/115 |
| 6,257,636 | B1 * | 7/2001 | Hovis | B66C 1/66 294/110.1 |
| 2012/0134769 | A1 * | 5/2012 | Friedman | G01N 35/0099 414/751.1 |

FOREIGN PATENT DOCUMENTS

| | | |
|---|---|---|
| JP | H02-66097 A | 3/1990 |
| JP | H02-152790 A | 6/1990 |
| JP | H02-114435 U | 9/1990 |
| JP | H04-70489 U | 6/1992 |
| JP | H04-106186 U | 9/1992 |
| JP | 2001-310285 A | 11/2001 |
| JP | 2002-370187 A | 12/2002 |
| JP | 2003-83992 A | 3/2003 |
| JP | 2009272171 A1 | 11/2009 |
| JP | 2012066357 A1 | 4/2012 |
| JP | 2013-501633 A | 1/2013 |
| JP | 2014-233765 A | 12/2014 |
| KR | 100824780 B1 | 4/2008 |
| WO | WO2007/039524 A2 | 4/2007 |

OTHER PUBLICATIONS

European Application No. 14805157.6; European Search Report and Opinion; 7 pgs; dated Dec. 14, 2016.

* cited by examiner

GRIPPING MECHANISM

TECHNICAL FIELD

The present invention relates to a gripping mechanism.

BACKGROUND ART

Conventionally, measurement apparatuses and methods are used to separate and identify a predetermined substance to be measured (hereinafter referred to as a target substance) from a sample containing a plurality of substances and to analyze the target substance. Such a measurement apparatus is provided with a transfer section that transfers a reaction container in which a sample is housed from a particular housing location to a transfer destination location. Furthermore, the transfer section is configured to include a gripping mechanism for gripping the reaction container.

As a configuration of the gripping mechanism, a configuration illustrated below has been proposed.

For example, Patent Document 1 discloses a mechanism including a holder that holds a reaction container, a rod portion having a tip portion that is fitted into the holder at an upper end opening of the reaction container, a rod holding section that elastically supports the rod portion such that the rod portion is slidable, and a guide section that surrounds the rod portion and that cancels the fitting of the transfer member by sliding the rod portion along an axis. Such a configuration allows the reaction container to be gripped by inserting the rod portion into the upper end opening of the reaction container. Then, the guide section presses the reaction container into which the rod portion has been inserted, to allow the reaction container to be removed.

Furthermore, Patent Document 2 discloses a mechanism including a pair of grip arms that holds the reaction container in a laterally sandwiching manner and a recess that is formed in each of the grip arms and that can be fitted over a neck portion of the reaction container. Such a configuration allows the reaction container to be gripped by reducing an interval between the pair of grip arms and fitting the recess over the neck portion of the reaction container. Then, the reaction container can be removed by increasing the interval between the pair of grip arms to cancel the fitting of the recess over the reaction container.

PRIOR ARTS

Patent Document 1: Japanese Patent Application Laid-open No. 2003-83992
Patent Document 2: WO 2007/039524

SUMMARY OF INVENTION

Problems to be Solved by Invention

It is an object of the present invention to solve the problems of the above mentioned prior arts.

Means to Solve Problems

One aspect of the present invention provides a gripping mechanism for gripping a gripping object, the gripping mechanism comprising: sandwiching means for holding the gripping object in a laterally sandwiching manner; pressing means for pressing downward an upper end surface of the gripping object held in a sandwiching manner by the sandwiching means, wherein the pressing means is arranged such that, with the gripping object being held in a sandwiching manner by the sandwiching means, a central axis of the gripping object along a vertical direction coincides mutually with a central axis of the pressing means in the vertical direction.

BRIEF DESCRIPTION OF THE DRAWINGS

FIG. 3 is a set of perspective views depicting a periphery of a gripping mechanism, in which

FIG. 5 is a set of diagrams depicting a gripping section holding a cuvette in a sandwiching manner, in which

FIG. 6 is a set of diagrams depicting the periphery of the gripping mechanism in a state where the gripping mechanism is gripping the cuvette, in which

FIG. 7 is a set of diagrams depicting the periphery of the gripping mechanism in a state where the gripping mechanism has released the cuvette, in which

FIG. 8 is a set of diagrams depicting the periphery of the gripping mechanism in a state where the gripping mechanism is closing the cuvette, in which

FIG. 10 is a set of plan views depicting a variation of the gripping mechanism.

MODE FOR CARRYING OUT THE INVENTION

With reference to the attached drawings, embodiments of a gripping mechanism according to the present invention will be described in detail. However, the embodiments do not limit the present invention. The gripping mechanism according to the present embodiment is applied to any targets. For example, in a medical field, the gripping mechanism according to the present embodiment is applicable to an automatic immunoassay apparatus that separates and identifies a target substance from a sample containing a plurality of types of substances and analyzes the target substance. In the present embodiment described below, a case will be described where the present invention is applied to an automatic immunoassay apparatus that analyzes samples such as blood using EIA (Enzyme Immunoassay) that uses an enzyme as a labeling substance. Furthermore, measuring apparatuses of this type include apparatuses that clean a reaction container after measurement and repeatedly use the reaction container for the next measurement and apparatuses that dispose of a disposable reaction container (hereinafter referred to as a cuvette) after measurement. The present invention can be applied to any of these apparatuses, but a case will described below where the present invention is applied to the latter apparatuses.

(Configuration)

Figure 1:
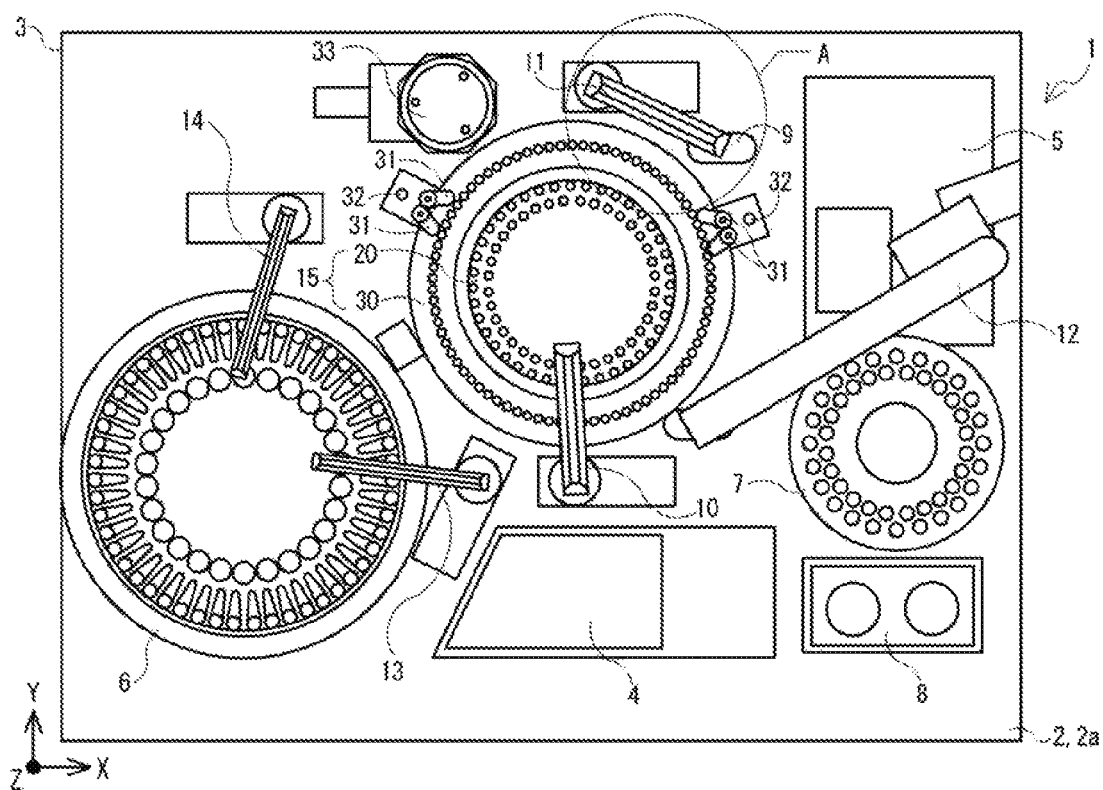
FIG. 1 is a plan view generally depicting a measurement apparatus according to the present embodiment.

First, a configuration of a measurement apparatus according to the present embodiment will be described. FIG. 1 is a plan view generally depicting the measurement apparatus according to the present embodiment. In the description below, an X direction in FIG. 1 corresponds to a lateral direction of the measurement apparatus. A Y direction in FIG. 1 corresponds to a front-rear direction of the measurement apparatus. A Z direction in FIG. 1 (a direction perpendicular to the sheet of FIG. 1) corresponds to an up-down direction of the measurement apparatus. Furthermore, in FIG. 1, illustration of a cover portion of a housing 2 described below is omitted for simplification of the drawing.

As depicted in FIG. 1, a measurement apparatus 1 is an automatic immunoassay apparatus and generally includes a measurement mechanism 3 inside the housing 2 on a base surface 2a thereof. The measurement mechanism 3 sequentially conveys a cuvette T to a plurality of predetermined positions where respective operations are performed for measurement. After the measurement, the cuvette T is disposed of. For the configuration of the measurement apparatus 1, a well-known automatic immunoassay apparatus may be adopted except for specified parts of the configuration. The cuvette T corresponds to a "gripping object" in the claims.

Furthermore, the measurement mechanism 3 includes a cuvette supply section 4, a chip supply section 5, a reagent storage section 6, a sample storage section 7, a substrate storage section 8, a cuvette disposal section 9, a first cuvette conveying section 10, a second cuvette conveying section 11, a sample conveying section 12, a first reagent dispensing section 13, a second reagent dispensing section 14, and a reaction tank 15.

The cuvette supply section 4 is housing alignment means in which a plurality of cuvettes T unused is housed in alignment with one another, and is configured as, for example, a parts feeder. The chip supply section 5 is chip housing alignment means in which disposal chips used to suck samples are housed in alignment with one another, and is configured, for example, using a chip rack in which a plurality of chips can be housed in alignment with one another. The reagent storage section 6 is reagent housing means in which containers containing a plurality of reagents (in this case, a magnet particle solution bottle, a labeled body fluid bottle, a pretreatment solution bottle, an analyte diluent bottle, and the like, none of which is illustrated) are housed in circular alignment with one another, and is configured using, for example, a reagent cooling box. The sample storage section 7 is sample housing means in which containers containing a plurality of samples are housed in circular alignment with one another, and is configured using, for example, a well-known sample cooling box. The substrate storage section 8 is substrate solution storage means in which a substrate solution is stored, and is configured using, for example, a well-known storage tank for substrate solutions. The cuvette disposal section 9 is a space portion that receives a cuvette T disposed of, and is arranged below the cuvette T conveyed by the second cuvette conveying section 11. The cuvette disposal section 9 corresponds to a "receiving space" in the claims.

The first cuvette conveying section 10 is cuvette conveying means for conveying the cuvette T housed in the cuvette supply section 4 to a first reaction line 20 to the reaction tank 15 described below. The second cuvette conveying section 11 is cuvette conveying means for conveying the cuvette T from the first reaction line 20 of the reaction tank 15 to a second reaction line 30 described below and conveying the cuvette T from the second reaction line 30 described below to the cuvette disposal section 9. The arrangement of the first cuvette conveying section 10 and the second cuvette conveying section 11 is such that, for example, the first cuvette conveying section 10 is positioned near the cuvette supply section 4 and the reaction tank 15 described below. Furthermore, the second cuvette conveying section 11 is positioned near the reaction tank 15 described below and the cuvette disposal section 9. The first cuvette conveying section 10 and the second cuvette conveying section 11 will be described below in detail. The first cuvette conveying section 10 and the second cuvette conveying section 11 correspond to "conveying means" in the claims.

The sample conveying section 12 is sample conveying means for acquiring a chip housed in the chip supply section 5, sucking the sample from the rack housed in the sample supply section via the chip and discharging the sucked sample into the cuvette T arranged in the first reaction line 20 described below. The first reagent dispensing section 13 is reagent dispensing means for dispensing a reagent from a container arranged in the reagent storage section 6 to the cuvette T arranged in the first reaction line 20 described below. The second reagent dispensing section 14 is reagent dispensing means for dispensing a reagent from a container arranged in the reagent storage section 6 to the cuvette T arranged in the second reaction line 30 described below. The sample conveying section 12, the first reagent dispensing section 13, and the second reagent dispensing section 14 each include a well-known robot arm using a step motor or the like and combined with a suction mechanism using a pump. Furthermore, the first reagent dispensing section 13 and the second reagent dispensing section 14 are arranged near the reagent storage section 6 and the reaction tank 15.

The reaction tank 15 is a conveying line through which a plurality of cuvettes T is conveyed, and is provided with the first reaction line 20 along an inner periphery of the reaction tank 15 and the second reaction line 30 along an outer periphery of the reaction tank 15. Treatments in the first reaction line 20 and the second reaction line 30 vary according to the type of a target substance. For example, the first reaction line 20 is a line in which pretreatment such as dilution is performed on the sample to allow the sample to react with magnetic particles. The second reaction line 30 is a line in which a marker is allowed to react with a reactant resulting from the reaction between the sample and the magnetic particles and which involves detection of enzyme reaction between the marker and a substrate and the amount of light resulting from chemical light emission from a product of the enzyme reaction. The first reaction line 20 and the second reaction line 30 are formed as concentrically arranged ring-like members. A plurality of hole portions is formed in each of the ring-like members such that the cuvette T is removably housed in the hole portion from above. Thus, the ring-like members can be rotated at the same conveying speed or at different conveying speeds (rotation speeds) via a well-known driving mechanism using a pulse motor or the like and not depicted in the drawings.

Furthermore, the second reaction line 30 is provided with a magnetism collecting section 31, a cleaning liquid discharging and sucking section 32, a plurality of stirring sections (not depicted in the drawings), and a substrate dispensing section (not depicted in the drawings). The magnetism collecting section 31 applies a magnetic force of an external magnet to the cuvette T to collect magnetic particles on inner wall surfaces of the cuvette T. The cleaning liquid discharging and sucking section 32 cleans the inside of the cuvette T of the magnetic particles by discharging a cleaning liquid fed from a cleaning liquid tank not depicted in the drawings, into the cuvette T via a pump and sucking the cleaning liquid via the pump. The plurality of stirring sections disperses the magnetic particles inside the cuvette T by rotating the cuvette T around a center axis of the cuvette T via a motor or vibrating the cuvette T via a vibrator. The substrate dispensing section dispenses a substrate solution fed from the substrate storage section 8 into the cuvette T via the pump not depicted in the drawings, and further after the dispensation of the substrate solution, stirs the cuvette T similarly to the plurality of stirring sections. Furthermore, after the magnetic particles and the substrate are allowed to react with one another in the second reaction line 30 for a predetermined time, the cuvette T is transferred to a measurement section 33 installed near the second reaction line 30. The measurement section 33 measures the amount of faint light resulting from chemical light emission from the product of the enzyme reaction, and more specifically, counts the number of photons using a photomultiplier tube.

(Configuration—Details of the First Cuvette Conveying Section and the Second Cuvette Conveying Section)

Figure 2:
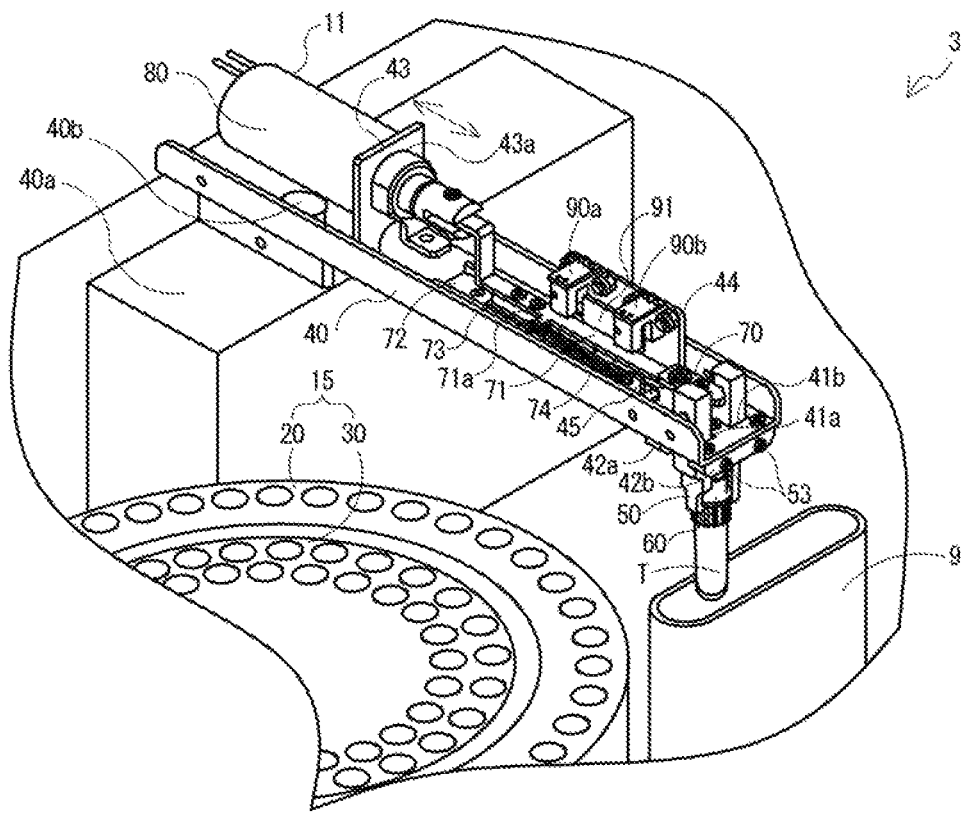
FIG. 2 is an enlarged perspective view of an area A in FIG. 1.
Figure 3A:
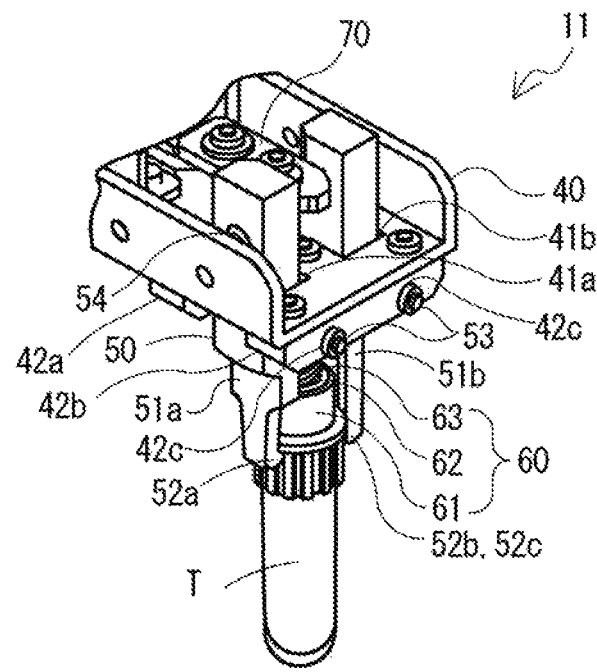
FIG. 3A is a diagram depicting a state where a cuvette is gripped by a gripping section.
Figure 3B:
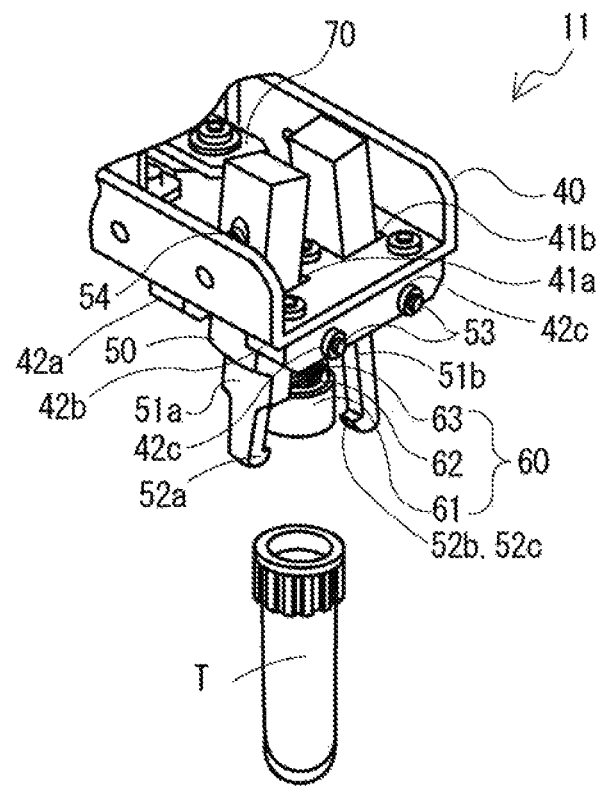
FIG. 3B is a diagram depicting a state where the cuvette is separated from the gripping section.
Figure 4:
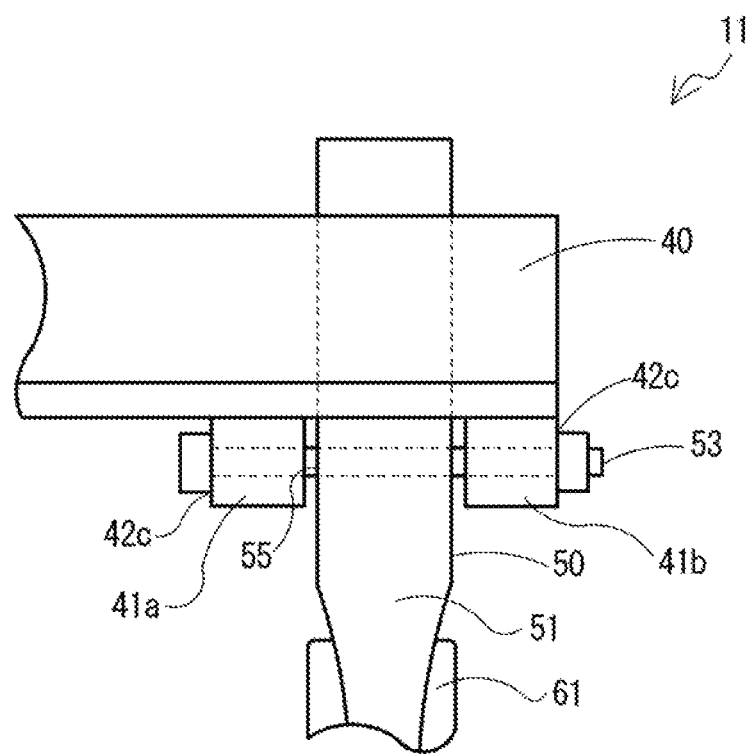
FIG. 4 is a side view depicting a periphery of the gripping mechanism.
Figure 5A:
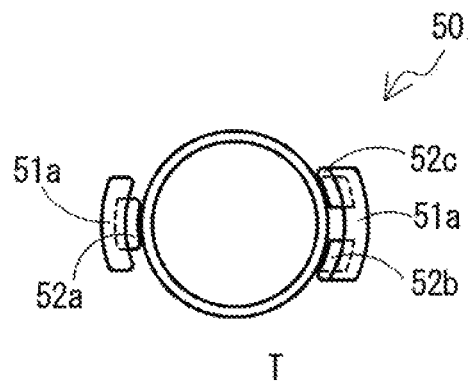
FIG. 5A is a plan view.
Figure 5B:
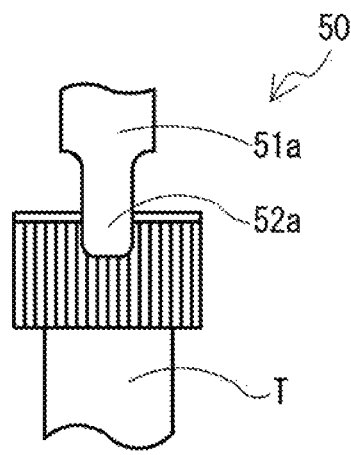
FIG. 5B is a side.
Figure 5C:
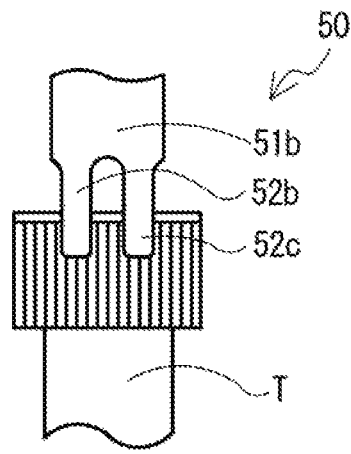
FIG. 5C is a side view of the gripping section as seen from a side opposite to the side from which the gripping section is seen in FIG. 5B.

Now, the first cuvette conveying section 10 and the second cuvette conveying section 11 according to the present embodiment will be described in detail. FIG. 2 is an enlarged perspective view of an area A in FIG. 1. FIG. 3 is a set of perspective views depicting a periphery of the gripping mechanism. FIG. 3A is a diagram depicting a state where the cuvette T is held by a sandwiching section 50 described below. FIG. 3B is a diagram depicting a state where the cuvette T is separated from the sandwiching section 50 described below. FIG. 4 is a side view depicting the periphery of the gripping mechanism. FIG. 5 is a set of diagrams depicting the sandwiching section 50 described below and holding the cuvette T in a sandwiching manner. FIG. 5A is a plan view, FIG. 5B is a side, and FIG. 5C is a side view of the sandwiching section 50 as seen from a side opposite to the side from which the sandwiching section is seen in FIG. 5B. In FIG. 5, illustration of a pressing section 60 described below is omitted for simplification of the drawings. Furthermore, the first cuvette conveying section 10 and the second cuvette conveying section 11 have substantially the same configuration. Thus, only the configuration of the second cuvette conveying section 11 will be described below. The second cuvette conveying section 11 is assumed to be configured as a well-known robot arm using a step motor or the like except for specified parts of the configuration. Additionally, a material for the various components of the second cuvette conveying section 11 is assumed to be a steel material or the like except for specified cases.

Specifically, as depicted in FIGS. 2 to 5A to 5C, the second cuvette conveying section 11 includes a support section 40, the sandwiching section 50, the pressing section 60, a wedge portion 70, a wedge driving section 80, a horizontal pivot driving section (not depicted in the drawings), an elevating and lowering driving section (not depicted in the drawings), and detection sections 90a, 90b. The sandwiching section 50, the pressing section 60, and the wedge portion 70 correspond to a "gripping mechanism" in the claims.

(Configuration—Details of the First Cuvette Conveying Section and the Second Cuvette Conveying Section—Support Section)

The support section 40 is support means for supporting the sandwiching section 50, the pressing section 60, the wedge portion 70, and the wedge driving section 80. The support section 40 is formed using an elongate plate-like member with a substantially recessed longitudinal sectional shape. The support section 40 is arranged on a pedestal 40a provided on the base surface 2a of the housing 2. More specifically, the support section 40 is connected to a rotating shaft 40b attached to the pedestal 40a using a screw threading structure or the like such that a longitudinal direction of the support section 40 is substantially horizontal.

Furthermore, the support section 40 is provided with openings 41a and 41b, rotating shaft fixing sections 42a, 42b, a wedge driving section fixing section 43, and a detection section fixing section 44.

The opening 41a is a through-hole through which an arm portion 51a of the sandwiching section 50 described below penetrates the support section 40. The opening 41b is a through-hole through which an arm portion 51b of the sandwiching section 50 described below penetrates the support section 40. The openings 41a, 41b are formed near one of the longitudinal ends of the support section 40 that is opposite to an end of the support section 40 closer to the pedestal 40a. More specifically, at a recessed bottom portion of the support section 40, the openings 41a, 41b are arranged in juxtaposition substantially along a transverse direction of the support section 40.

The rotating shaft fixing sections 42a, 42b are members that fix rotating shafts 53 supporting the arm portions 51a, 51b of the sandwiching section 50 described below such that the rotating shafts 53 are rotatable. The rotating shaft fixing sections 42a, 42b are formed using generally columnar members and arranged near one of the longitudinal ends of the support section 40 that is closer to the end of the support section 40 closer to the pedestal 40a. More specifically, as depicted in FIG. 4, the rotating shaft fixing sections 42a, 42b are arranged to protrude downward toward the recessed bottom portion of the support section 40 and arranged away from each other in juxtaposition substantially along the longitudinal direction of the support section 40. The rotating shaft fixing sections 42a, 42b have openings 42C through which the rotating shafts 53 of the respective arm portions 51a, 51b of the sandwiching section 50 described below are inserted.

The wedge driving section fixing section 43 is a member that fixes the wedge driving section 80. The wedge driving section fixing section 43 is formed using a substantially plate-like member. Furthermore, the wedge driving section fixing section 43 is arranged on a side of the support section 40 that is closer to the pedestal 40a. More specifically, the wedge driving section fixing section 43 is arranged to protrude upward with respect to the recessed bottom portion of the support section 40 and arranged substantially along the transverse direction of the support section 40. The wedge driving section fixing section 43 has an opening 43a through which a piston of the wedge driving section 80 is inserted.

The detection section fixing section 44 is a member that fixes detection sections 90a, 90b. The detection section fixing section 44 is formed using a substantially plate-like member. Furthermore, the detection section fixing section 44 is arranged between the wedge driving section fixing section 43 and the rotating shaft fixing sections 42a, 42b. More specifically, the detection section fixing section 44 is arranged to protrude upward with respect to the recessed bottom portion of the support section 40 and arranged substantially along the longitudinal direction of the support section 40.

(Configuration—Details of the First Cuvette Conveying Section and the Second Cuvette Conveying Section—Sandwiching Section)

The sandwiching section 50 is sandwiching means for holding the cuvette in a laterally sandwiching manner. The sandwiching section 50 is formed of, for example, a resin material and arranged near one of the longitudinal ends of the support section 40 that is opposite to the end of the support section 40 that is closer to the pedestal 40*a*. Furthermore, the sandwiching section 50 includes the arm portions 51*a*, 51*b* and pawl portions 52*a* to 52*c* (the arm portions 51*a*, 51*b* are collectively referred to as the "arm portion 51" when the arm portions 51*a*, 51*b* need not be distinguished from each other, and the pawl portions 52*a* to 52*c* are collectively referred to as the "pawl portion 52" when the pawl portions 52*a* to 52*c* need not be distinguished from each other). Any formation method may be used for the sandwiching section 50. For example, a method may be used in which the arm portion 51*a* and the pawl portion 52*a* are integrated together and in which the arm portion 51*b* and the pawl portions 52*b*, 52*c* are integrated together.

The arm portions 51*a*, 51*b* are formed using substantially rod-like members and arranged so as to penetrate openings 41*a*, 41*b*, respectively, in the support section 40. As depicted in FIG. 4, an opening 55 is formed in each of the arm portions 51*a*, 51*b*, and the arm portions 51*a*, 51*b* are rotatably connected to the rotating shaft fixing sections 42*a*, 42*b* of the support section 40 via the rotating shaft 53 inserted through the opening 55. In this case, the position where the opening is formed is optional. For example, the opening 55 may be formed at an upper end of each of the arm portions 51*a*, 51*b*. However, in the present embodiment, the openings 55 are formed in substantially central portions of the respective arm portions 51*a*, 51*b* such that the wedge portion 70 is inserted into the arm portions 51*a*, 51*b* at the upper ends thereof in order to allow the tilt of the arm portions 51*a*, 51*b* to be controlled.

Furthermore, each of the arm portions 51*a*, 51*b* is provided with a first biasing section 54. The first biasing section 54 does not bias the arm portion 51*a* (or the arm portion 51*b*) while the cuvette T is located away from the sandwiching section 50 (for example, a state depicted in FIG. 3B. The first biasing section 54 biases the arm portion 51*a* toward the arm portion 51*b* (or biases the arm portion 51*b* toward the arm portion 51*a*) while the cuvette T is held in a sandwiching manner by the sandwiching section 50 (for example, a state depicted in FIG. 3A. The first biasing section 54 is formed using, for example, an elastic spring member (for example, a coil spring) (this also applies to a second biasing section 63 of the pressing section 60 described below and a third biasing section 74 of a coupling portion 71 described below). Additionally, the first biasing section 54 is arranged between the support section 40 and the arm portion 51*a* (or between the support section 40 and the arm portion 51*b*) and fixed to the support section 40 and the arm portion 51*a* (or the support section 40 and the arm portion 51*b*) using a fixture or the like.

The pawl portions 52*a* to 52*c* are members that come into abutting contact with the cuvette T. The pawl portions 52*a* to 52*c* are formed using a substantially plate-like member. The pawl portion 52*a* is connected to a lower end of the arm portion 51*a*. The pawl portions 52*b*, 52*c* are connected to a lower end of the arm portion 51*b*.

The arrangement of the pawl portions 52*a* to 52*c* is optional. For example, the pawl portions 52*a* to 52*c* are preferably arranged so as to enable centering of the cuvette T by coming into abutting contact with the cuvette T. Specifically, the pawl portions 52*a* to 52*c* are arranged such that, with the cuvette T held in a sandwiching manner by the sandwiching section 50, a central position of a virtual circle is located on a central axis of the cuvette T along the Z direction, the virtual circle being formed substantially along a part of each of the pawl portions 52*a* to 52*c* that is in abutting contact with the cuvette T and circumscribing the pawl portions 52*a* to 52*c* as depicted in FIGS. 5A to 5C. In other words, a virtual circle is set which is concentric with the central axis of the cuvette T along the Z direction, and three points are set which contact an outer circumference of the virtual circle and which are spaced at intervals, with the pawl portions 52*a* to 52*c* arranged at these three points. Furthermore, the shapes of the pawl portions 52*a* to 52*c* are optional. For example, tip portions of the pawl portions 52*a* to 52*c* are formed like circular arcs extending substantially along the outer circumference of the virtual circle and each shaped generally like a hook so as to be engageable with a neck portion of the cuvette T as depicted in FIGS. 3A and 3B.

(Configuration—Details of the First Cuvette Conveying Section and the Second Cuvette Conveying Section—Pressing Section)

The pressing section 60 is pressing means for pressing downward an upper end surface of the cuvette T held in a sandwiching manner by the sandwiching section 50. The pressing section 60 is arranged between the arm portions 51*a*, 51*b* of the sandwiching section 50 and includes a head portion 61, a guide section 62, and a second biasing section 63.

The head portion 61 is a member that comes into abutting contact with the upper end surface of the cuvette T. The head portion 61 is a generally cylindrical member formed of, for example, a resin material. Furthermore, the head portion 61 is arranged such that a central axis of the head portion 61 extends substantially along the Z direction. In this case, the shape of the head portion 61 is optional. For example, an outer edge shape of the head portion 61 is set similar to an outer edge shape of an upper end surface of the cuvette T in order to enable suppression of eccentricity resulting from pressing of the cuvette T. The head portion 61 corresponds to a "part of the pressing means that is in abutting contact with the gripping object" in the claims. Additionally, the upper end surface of the cuvette T corresponds to a "part of the gripping object that is in abutting contact with the pressing means" in the claims.

The guide section 62 is guide means for guiding the head portion 61 substantially along the Z direction. The guide section 62 is a substantially elongate rod-like member and is inserted through the head portion 61 such that a longitudinal direction of the guide section 62 extends substantially along the Z direction. An upper end of the guide section 62 is fixed to the support section 40 using a fixture or the like. On the other hand, a stopper 64 is provided at a lower end of the guide section 62 to prevent the head portion 61 from falling down from the guide section 62.

The second biasing section 63 is bias means for biasing the head portion 61 downward. The second biasing section 63 is arranged concentrically with the guide section 62 so as to surround an outer edge of the guide section 62.

The arrangement of the pressing section 60 configured as described above is optional. For example, the pressing section 60 is preferably arranged so as to enable the orientation of the cuvette T to be stabilized. Specifically, the pressing section 60 is arranged such that, with the cuvette T held in a sandwiching manner by the sandwiching section 50, the central axis of the cuvette T along the Z direction coincides with a central axis of the pressing section 60 along the Z direction (specifically, a central axis of the head portion 61 along the Z direction, a central axis of the guide section 62 along the Z direction, and a central axis of the second biasing section 63 along the Z direction).

(Configuration—Details of the First Cuvette Conveying Section and the Second Cuvette Conveying Section—Wedge Portion)

The wedge portion 70 is intended to switch a tilt state of the arm portions 51a, 51b by being inserted into a part between the arm portions 51a, 51b that extends from ends of the arm portions 51a, 51b opposite to ends of the arm portions 51a, 51b closer to the cuvette T to the rotating shafts 53 (hereinafter referred to as the insertion part of the arm portions 51a, 51b). The wedge portion 70 is formed using a substantially elongate plate-like member. Furthermore, the wedge portion 70 is positioned near the upper ends of the arm portions 51a, 51b. More specifically, the wedge portion 70 is arranged such that a longitudinal direction of the wedge portion 70 extends substantially along a longitudinal direction of the support section 40 and such that side surfaces of the wedge portion 70 extend substantially horizontally.

In this regard, the shape of the wedge portion 70 is formed to enable the tilt state of the arm portions 51a, 51b to be switched, for example, based on the amount of insertion of the wedge portion 70 into the insertion part of the arm portions 51a, 51b. Specifically, an end of the wedge portion 70 closer to the arm portions 51a, 51b is shaped to have acute angles such that the interval between the upper ends of the arm portions 51a, 51b increases consistently with the amount by which the wedge portion 70 is inserted. In this regard, since the arm portions 51a, 51b are rotatably supported near the centers thereof in the longitudinal direction via the rotating shafts 53 as described above, a change in the interval between the upper ends of the arm portions 51a, 51b changes, in the opposite direction, the interval between the pawl portions 52 located at the lower portions of the arm portions 51a, 51b. In other words, increasing the insertion amount of the wedge portion 70 reduces the interval between the pawl portions 52, whereas reducing the insertion amount of the wedge portion 70 increases the interval between the pawl portions 52. Thus, the interval between the pawl portions 52 can be adjusted by the insertion amount of the wedge portion 70.

In this case, for the width of the wedge portion 70, for example, the minimum width of the wedge portion 70 is set so as to make the interval between the pawl portions 52 supported by the arm portions 51a, 51b larger than the width of the cuvette T. Furthermore, the maximum width of the wedge portion 70 is set to a value at which the interval between the pawl portions 52 supported by the arm portions 51a, 51b is smaller than the width of the cuvette T. Additionally, an intermediate width of the wedge portion 70 between the minimum width and the maximum width is set such that the interval between the pawl portions 52 supported by the arm portions 51a, 51b is substantially equal to the width of the cuvette T. The shapes of the arm portions 51a, 51b are optional. For example, for an end surface of each of the arm portions 51a, 51b, a part of the end surface that is in abutting contact with the wedge portion 70 may be tilted in order to facilitate the insertion of the wedge portion 70 into the insertion part of the arm portions 51a, 51b.

(Configuration—Details of the First Cuvette Conveying Section and the Second Cuvette Conveying Section—Wedge Driving Section, Horizontal Pivot Driving Section, and Elevating and Lowering Driving Section)

The wedge driving section 80 is wedge driving means for adjusting, via the coupling portion 71, the amount of insertion of the wedge portion 70 into the insertion part of the arm portions 51a, 51b of the sandwiching section 50. The wedge driving section 80 is configured using a well-known solenoid or the like. Furthermore, the wedge driving section 80 is arranged closer to the pedestal 40a of the support section 40. More specifically, the wedge driving section 80 is arranged at a position where a piston of the wedge driving section 80 is inserted into the opening 43a in the wedge driving section fixing section 43. The piston of the wedge driving section 80 is fixed to the wedge driving section fixing section 43 using a screw threading structure or the like. The horizontal pivot driving section and the elevating and lowering driving section are arranged near the wedge driving section 80 configured as described above. The horizontal pivot driving section pivots the support section 40 around the rotating shaft 40b. The elevating and lowering driving section elevates and lowers the support section 40 via the rotating shaft 40b. The horizontal pivot driving section and the elevating and lowering driving section are configured using, for example, well-known motors.

Furthermore, the wedge driving section 80 is provided with the coupling portion 71 and a rail portion 72.

The coupling portion 71 is formed using an elongate plate-like member and arranged substantially along the longitudinal direction of the support section 40. One longitudinal end of the coupling portion 71 is connected to the wedge portion 70. The other longitudinal end of the coupling portion 71 is connected to the piston of the wedge driving section 80. Furthermore, the coupling portion 71 is provided with a third biasing section 74. The third biasing section 74 is bias means for biasing, in a default state described below, the coupling portion 71 such that the wedge portion 70 is inserted into the insertion part of the arm portions 51a, 51b. Specifically, one longitudinal end of the third biasing section 74 is fixed to a projecting portion 71a projecting from the coupling portion 71. The other longitudinal end of the third biasing section 74 is fixed to a biasing section fixing section 45 provided on the support section 40. The third biasing section 74 biases the wedge portion 70 in the direction in which the wedge portion 70 is inserted between the arm portions 51a, 51b. Thus, if the measurement apparatus 1 is powered off due to power outage, the gripping mechanism is used to grip the cuvette T to allow the cuvette T to be prevented from falling down.

The rail portion 72 is an elongate member with a recessed longitudinal sectional shape and is fixed to the recessed bottom portion of the support section 40. In this regard, with a slide block 73 being fixed to a lower surface of the coupling portion 71 along this coupling portion 71, and this slide block 73 being configured to slide inside and along the rail portion 72, the coupling portion 71 moves along the longitudinal direction of the support section 40. The rail portion 72 is provided with a bearing (not depicted in the drawings) intended to smooth the sliding of the slide block 73.

(Configuration—Details of the First Cuvette Conveying Section and the Second Cuvette Conveying Section—Detection Section)

The detection sections 90a, 90b are detection means for detecting the amount of movement of the coupling portion 71 in order to detect the tilt state of the arm portions 51a, 51b of the sandwiching section 50. The detection sections 90a, 90b are arranged near the coupling portion 71 and fixed to the detection section fixing section 44.

Furthermore, the detection sections 90a, 90b are configured using well-known distance sensors (for example, optical distance measurement sensors). More specifically, the detection sections 90a, 90b are configured as what is called forked sensors with generally U-shaped side surfaces. An optical path of an optical element (not depicted in the drawings) provided inside each of the detection sections 90a, 90b is blocked by a light shielding plate 91 erected upward from the coupling portion 71 to enable the position of the coupling portion 71 to be detected. That is, as a combination of the state of detection of the light shielding plate 91 by the detection section 90a and the state of detection of the light shielding plate 91 detected by the detection section 90b, the following three detection states may be assumed. A first detection state is a state where the detection section 90a detects the light shielding plate 91 ("detection by the detection section 90a =ON") and where the detection section 90b fails to detect the light shielding plate 91 ("detection by the detection section 90b=OFF"). In the first detection state, the amount by which the wedge portion 70 is inserted is minimized, meaning that the distances between the pawl portion 52a and the pawl portions 52b and 52c are maximized. A second detection state is a state where the detection section 90a detects the light shielding plate 91 ("detection by the detection section 90a=ON") and where the detection section 90b also detects the light shielding plate 91 ("detection by the detection section 90b=ON"). In the second detection state, the insertion amount of the wedge portion 70 falls between the minimum value and the maximum value, meaning that the mutual interval between the pawl portions 52a to 52c falls between the minimum value and the maximum value. A third detection state is state where the detection section 90a fails to detects the light shielding plate 91 ("detection by the detection section 90a=OFF") and where the detection section 90b detects the light shielding plate 91 ("detection by the detection section 90b=ON"). In the third detection state, the amount by which the wedge portion 70 is inserted is maximized, meaning that the distances between the pawl portion 52a and the pawl portions 52b and 52c are minimized. Therefore, a control section (not depicted in the drawings) of the measurement apparatus 1 determines to which of the three detection states the current state corresponds based on outputs from the detection sections 90a, 90b, enabling determination of the insertion amount of the wedge portion 70 and the mutual interval between the pawl portion 52a and the pawl portions 52b and 52c.

Specific timings for such determinations are optional, but the determination may be made each time the position of the gripping mechanism changes. For example, when the second cuvette conveying section 11 is used to convey the cuvette T from the second reaction line 30 to the cuvette disposal section 9, the control section (not depicted in the drawings) of the measurement apparatus 1 makes the determination at the following timings. First, the determination is made at a timing when the gripping mechanism is lowered to a predetermined position in order to grip the cuvette T housed in the hole portion in the second reaction line 30. Then, the determination is made at a timing when the gripping mechanism is elevated to a predetermined position in order to raise the gripped cuvette T. Then, the determination is made at a timing when the gripping mechanism is moved to the cuvette disposal section 9 in order to convey the cuvette T to the cuvette disposal section 9. Finally, after the cuvette T is disposed of at the cuvette disposal section 9, the determination is made at a timing when the gripping mechanism is moved to a predetermined position in order to return the gripping mechanism. Moreover, even during these operations, the determination may be made immediately after the cuvette T is gripped or released.

Each time the determination is made at such a timing, the control section (not depicted in the drawings) of the measurement apparatus 1 determines whether or not the insertion amount of the wedge portion 70 and the mutual interval between the pawl portion 52a and the pawl portions 52b and 52c are in predetermined states. When the insertion amount and the mutual interval are not in the predetermined states, the control section performs error control. Thus, a storage section (not depicted in the drawings) of the measurement apparatus 1 pre-stores a determination table in which each position of the gripping mechanism is associated with a predetermined state at the position (one of the above-described three states). Each time the position of the gripping mechanism changes, the control section determines whether or not the state determined based on the outputs from the detection sections 90a, 90b matches a predetermined state stored in the determination table in association with the changed position. When the determined state matches the predetermined state, the control section determines that the insertion amount of the wedge portion 70 and the mutual interval between the pawl portion 52a and the pawl portions 52b and 52c are in normal states and continues the control without any change. On the other hand, when the determined state fails to match the predetermined state, the control section determines that the insertion amount of the wedge portion 70 and the mutual interval between the pawl portion 52a and the pawl portions 52b and 52c are in abnormal states and performs predetermined error control. The specific contents of the error control are optional. For example, the cuvette T may fail to be normally transferred leading to an unstable gripping state of the cuvette T or the cuvette T may have fallen down on a conveying path. Thus, the operation of the first cuvette conveying section 10 (or the second cuvette conveying section 11) is stopped or information indicative of occurrence of a detection error is output by output means (not depicted in the drawings) of the measurement apparatus (for example, display means such as a display or audio output means such as a speaker).

(Operations of the First Cuvette Conveying Section and the Second Cuvette Conveying Section)

Figure 6A:
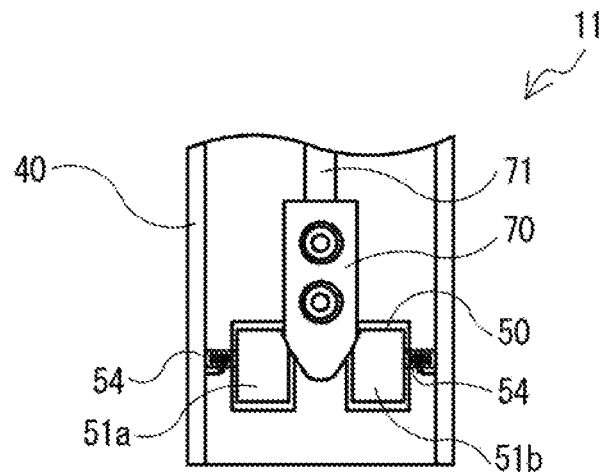
FIG. 6A is a plan view.
Figure 6B:
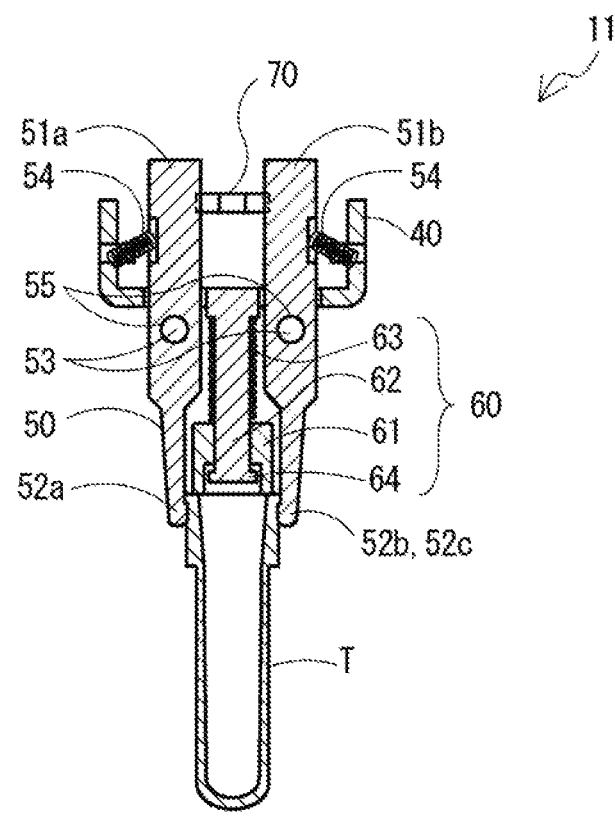
FIG. 6B is a front sectional view.
Figure 7A:
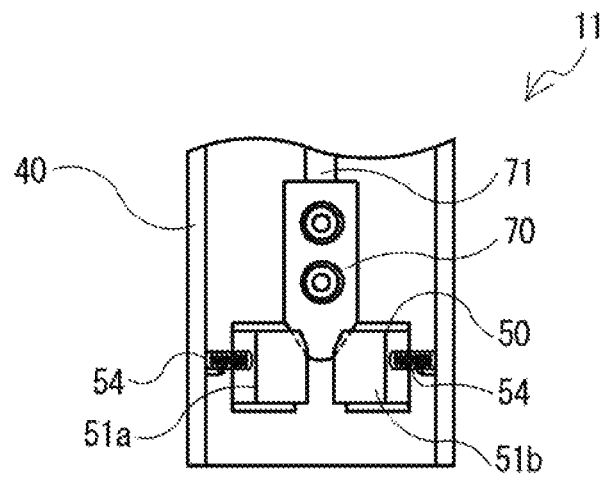
FIG. 7A is a plan view.
Figure 7B:
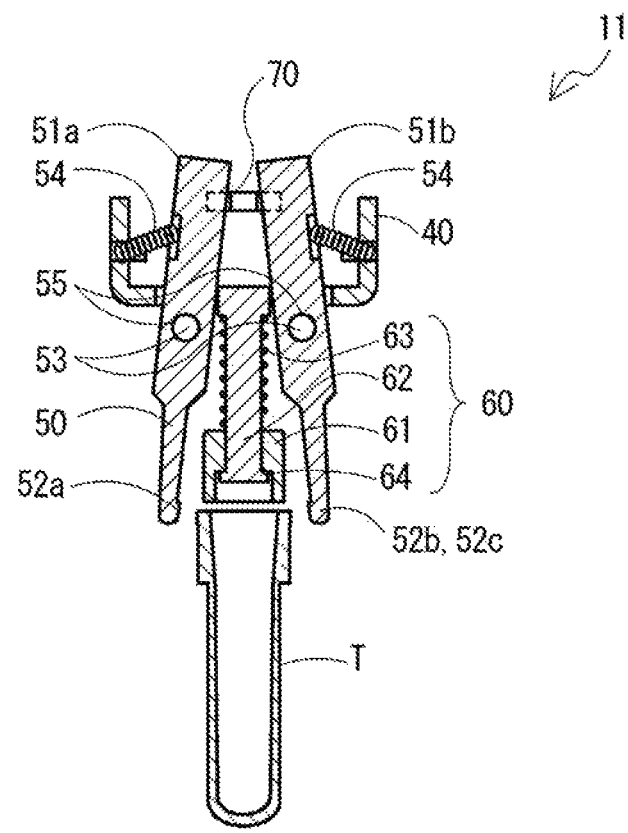
FIG. 7B is a front sectional view.
Figure 8A:
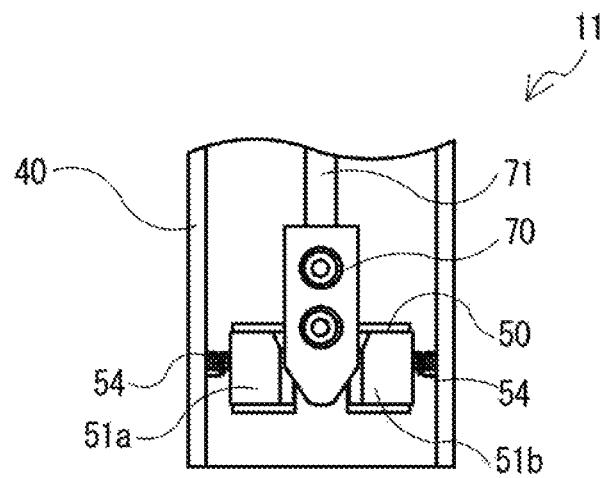
FIG. 8A is a plan view.
Figure 8B:
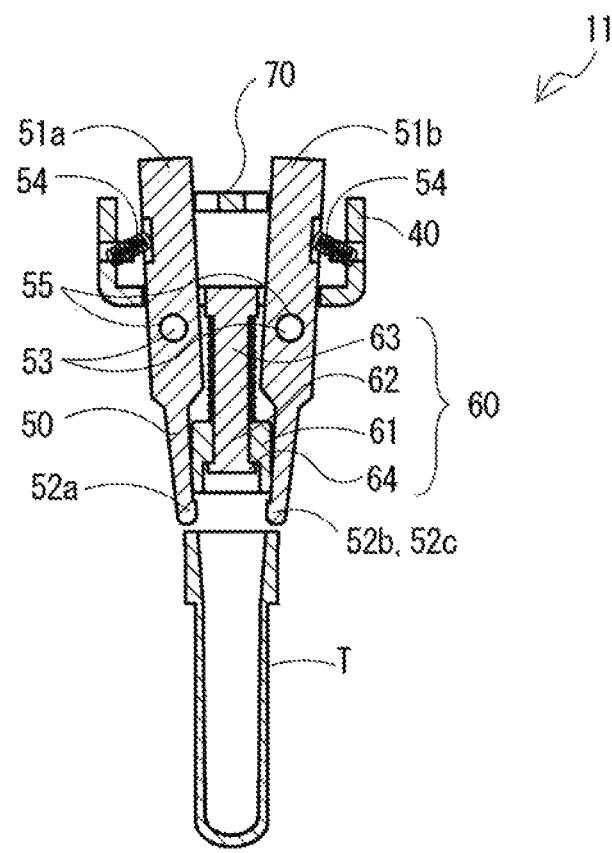
FIG. 8B is a front sectional view.

Now, operations of the first cuvette conveying section 10 and the second cuvette conveying section 11 configured as described above will be described. FIG. 6 is a set of diagrams depicting a periphery of the gripping mechanism in a state where the gripping mechanism is gripping the cuvette T. FIG. 6A is a plan view, and FIG. 6B is a front sectional view. FIG. 7 is a set of diagrams depicting the periphery of the gripping mechanism in a state where the gripping mechanism has released the cuvette T. FIG. 7A is a plan view, and FIG. 7B is a front sectional view. FIG. 8 is a set of diagrams depicting the periphery of the gripping mechanism in a state where the gripping mechanism is closing the cuvette T. FIG. 8A is a plan view, and FIG. 8B is a front sectional view. The operation of the first cuvette conveying section 10 is substantially the same as the operation of the second cuvette conveying section 11, and thus, only the operation of the second cuvette conveying section 11 will be described below. Furthermore, a method for operating the second cuvette conveying section 11 of is optional. For example, upon accepting a predetermined start instruction from a user via input means not depicted in the drawings, the control section of the measurement apparatus interprets and executes a measurement program installed in the storage section of the measurement apparatus 1 to automatically operate the second cuvette conveying section 11.

Furthermore, the operation of the second cuvette conveying section 11 is divided into two operations, a "gripping operation" of gripping the cuvette T and a "releasing operation" of cancelling the gripping of the cuvette T by the second cuvette conveying section 11 (specifically the gripping mechanism). In this regard, timings when the second cuvette conveying section 11 performs the "gripping operation" correspond to, for example, a timing when the cuvette T housed in the hole portion in the first reaction line 20 in the reaction tank 15 is gripped if the cuvette T is transferred from the first reaction line 20 to the second reaction line 30 and a timing when the cuvette T housed in the hole portion in the second reaction line 30 is gripped if the cuvette T is transferred from the second reaction line 30 to the cuvette disposal section 9. Additionally, timings when the second cuvette conveying section 11 performs the "releasing operation" correspond to, for example, a timing when the gripping of the cuvette T by the second cuvette conveying section 11 is cancelled at the second reaction line 30 if the cuvette T is transferred from the first reaction line 20 to the second reaction line 30 and a timing when the gripping of the cuvette T by the second cuvette conveying section 11 is cancelled at the cuvette disposal section 9 if the cuvette T is transferred from the second reaction line 30 to the cuvette disposal section 9.

Furthermore, the state of the gripping mechanism in the "gripping operation" or the "releasing operation" of the second cuvette conveying section 11 includes three states, a "state where the cuvette T is gripped", a "state where the cuvette T is released", and a "state where the cuvette T is closed". In this regard, the "state where the cuvette T is gripped" is a state where the gripping mechanism is gripping the cuvette T as depicted in FIGS. 6A and 6B. The "state where the cuvette T is released" is a state where the gripping mechanism does not grip the cuvette T and where the pawl portions 52 supported by the arm portions 51*a*, 51*b* of the sandwiching section 50 are more separate from one other than in the "state where the cuvette T is gripped" as depicted in FIGS. 7A and 7B. The "state where the cuvette T is closed" is a state where the gripping mechanism is not gripping the cuvette T and where the pawl portions 52 supported by the arm portions 51*a*, 51*b* are closer to one another than in the "state where the cuvette T is gripped" as depicted in FIGS. 8A and 8B. The "state where the cuvette T is closed" can be maintained if the measurement apparatus 1 is powered off due to power outage or the like with the gripping mechanism gripping the cuvette T, thus preventing the cuvette T from falling down. Therefore, in the present embodiment, the "state where the cuvette T is closed" is a "default state" of the gripping mechanism.

Timings when the "default state" is entered include, for example, an initial state of the "gripping operation" and an end state of the "release operation". Furthermore, in a specific state, the wedge portion 70 is inserted into the insertion part of the arm portions 51*a*, 51*b* so as to maximize the amount of insertion of the wedge portion 70 into the insertion part as depicted in FIGS. 8A and 8B. Additionally, the arm portions 51*a*, 51*b* are tilted so as to make the interval between the pawl portions 52 supported by the arm portions 51*a*, 51*b* smaller than the width of the cuvette T (in this case, the first biasing section 54 exerts a bias force). Moreover, the head portion 61 is in abutting contact with the stopper 64 of the guide section 62.

(Operations of the First Cuvette Conveying Section and the Second Cuvette Conveying Section—Gripping Operation)

First, the gripping operation included in the operation of the second cuvette conveying section 11 will be described.

First, if, for example, the cuvette T is conveyed from the second reaction line 30 to the cuvette disposal section 9, then at a timing when the cuvette T housed in the hole portion in the second reaction line 30 is gripped, the control section of the measurement apparatus 1 uses the horizontal pivot driving section to pivot the second cuvette conveying section 11 toward the second reaction line 30.

Then, the control section of the measurement apparatus 1 performs control that shifts the state of the gripping mechanism from the default state to the state where the cuvette T is released. Specifically, the control section of the measurement apparatus 1 uses the wedge driving section 80 to move the wedge portion 70 until the light shielding by the light shielding plate 91 is detected only by the detection section 90*a* (in other words, to the position where the amount of insertion of the wedge portion 70 into the insertion part of the arm portions 51*a*, 51*b* is minimized).

Thus, as depicted in FIGS. 7A and 7B, the arm portions 51*a*, 51*b* are tilted so as to make the interval between the pawl portions 52 supported by the arm portions 51*a*, 51*b* larger than the width of the cuvette T (this tilt state is hereinafter referred to as the "first state". In this case, the first biasing section 54 exerts no bias force). Furthermore, the head portion 61 is kept in abutting contact with the stopper 64. That is, the gripping mechanism is in the state where the gripping mechanism has released the cuvette T.

Then, the control section of the measurement apparatus 1 uses the elevating and lowering driving section to lower the second cuvette conveying section 11 to a position where a predetermined cuvette T housed in the second reaction line 30 can be gripped. In this regard, the "position where the cuvette T can be gripped" means a position where the head portion 61 moves upward along the guide section 62 in abutting contact with the upper end surface of the cuvette T and where the second biasing section 63 of the pressing section 60 biases the cuvette T downward.

Subsequently, the control section of the measurement apparatus 1 performs control that shifts the state of the gripping mechanism from the state where the cuvette T is released to the state where the cuvette T is gripped. Specifically, the control section of the measurement apparatus 1 uses the wedge driving section 80 to move the wedge portion 70 until the light shielding by the light shielding plate 91 is detected by the detection sections 90*a*, 90*b* (in other words, to the position where the amount of insertion of the wedge portion 70 into the insertion part of the arm portions 51*a*, 51*b* falls between the minimum value and the maximum value).

Thus, as depicted in FIGS. 6A and 6B, the arm portions 51*a*, 51*b* are tilted so as to make the interval between the pawl portions 52 supported by the arm portions 51*a*, 51*b* substantially equal to the width of the cuvette T (this tilt state is hereinafter referred to as the "second state". In this case, the first biasing section 54 exerts a bias force). Furthermore, the head portion 61 presses downward the upper end surface of the cuvette T sandwiched between the arm portions 51*a*, 51*b* due to the bias force of the second biasing section 63. That is, the gripping mechanism is in the state where the gripping mechanism is gripping the cuvette T. In this case, the central axis of the cuvette T along the Z direction coincides with the central axis of the pressing section 60 along the Z direction, allowing the orientation of the cuvette T to be effectively stabilized. Additionally, the pawl portions 52a to 52c are arranged such that the central position of a virtual circle circumscribing the pawl portions 52a to 52c lies on the central axis of the cuvette T along the Z direction, and thus, the pawl portions 52a to 52c come into abutting contact with the cuvette T to enable centering of the cuvette T. In addition, the shape of the head portion 61 is similar to the shape of the upper end surface of the cuvette T, enabling suppression of eccentricity resulting from pressing of the cuvette T.

Then, the control section of the measurement apparatus 1 uses the elevating and lowering driving section to elevate the second cuvette conveying section 11 to a position to which the cuvette T can be conveyed from the second reaction line 30. In this regard, the "position to which the cuvette T can be conveyed from the second reaction line 30" means a position where the lower end of the cuvette T lies above the second reaction line 30. Thus, the gripping operation of the second cuvette conveying section 11 ends.

(Operations of the First Cuvette Conveying Section and the Second Cuvette Conveying Section—Releasing Operation)

Now, the releasing operation, included in the operation of the second cuvette conveying section 11, will be described below.

First, if, for example, the cuvette T is conveyed from the second reaction line 30 to the cuvette disposal section 9, then at a timing when the gripping of the cuvette T by the second cuvette conveying section 11 is cancelled at the cuvette disposal section 9, the control section of the measurement apparatus 1 uses the horizontal pivot driving section to pivot the second cuvette conveying section 11 toward the cuvette disposal section 9.

Then, the control section of the measurement apparatus 1 performs control that shifts the state of the gripping mechanism from the state where the cuvette T is gripped to the state where the cuvette T is released. Specifically, the control section of the measurement apparatus 1 uses the wedge driving section 80 to move the wedge portion 70 until the light shielding by the light shielding plate 91 is detected only by the detection section 90a.

Thus, as depicted in FIGS. 7A and 7B, the arm portions 51a, 51b are tilted as in the first state. Furthermore, with the tilt of the arm portions 51a, 51b changed, the head portion 61 moves downward to a position where the head portion 61 comes into abutting contact with the stopper 64 due to the bias force of the second biasing section 63. That is, the gripping mechanism is in the state where the gripping mechanism has released the cuvette T. In this case, the releasing operation performed by the second cuvette conveying section 11 above the cuvette disposal section 9 enables the head portion 61 subjected to the bias force of the second biasing section 63 to push the cuvette T downward. Thus, the gripping of the cuvette T by the second cuvette conveying section 11 can be easily released.

Then, the control section of the measurement apparatus 1 performs control that shifts the state of the gripping mechanism from the state the cuvette T is released to the default state. Specifically, the control section of the measurement apparatus 1 uses the wedge driving section 80 to move the wedge portion 70 until the light shielding by the light shielding plate 91 is detected only by the detection section 90b (in other words, to a position where the amount of insertion of the wedge portion 70 into the insertion part of the arm portions 51a, 51b is maximized).

Thus, as depicted in FIGS. 8A and 8B, the arm portions 51a, 51b are tilted so as to make the interval between the pawl portions 52 supported by the arm portions 51a, 51b smaller than the width of the cuvette T. Furthermore, the head portion 61 is kept in abutting contact with the stopper 64. That is, the gripping mechanism is in the default state. Then, the releasing operation of the second cuvette conveying section 11 ends.

(Effects)

As described above, the present embodiment includes the sandwiching section 50 holding the cuvette T in a laterally sandwiching manner and the pressing section 60 that presses the upper end surface of the cuvette T downward which is held in a sandwiching manner by the sandwiching section 50. This prevents the sandwiching section 50 and the pressing section 60 from entering the inside of the cuvette T, enabling suppression of possible static electricity and possible contamination in the cuvette T. Furthermore, the pressing section 60 is arranged such that, with the cuvette T held in a sandwiching manner by the sandwiching section 50, the central axis of the cuvette T along the Z direction coincides with the central axis of the pressing section 60 along the Z direction. Thus, the orientation of the cuvette T can be effectively stabilized to enable the first cuvette conveying section 10 (or the second cuvette conveying section 11) to appropriately convey the cuvette T.

Furthermore, the pawl portions 52a to 52c are arranged such that, with the cuvette T held in a sandwiching manner by the sandwiching section 50, the central position of the virtual circle is located on the central axis of the cuvette T along the Z direction, the virtual circle being formed substantially along the part of each of the pawl portions 52a to 52c of the sandwiching section in abutting contact with the cuvette T and circumscribing the pawl portions 52a to 52c. Thus, the pawl portions 52a to 52c come into abutting contact with the cuvette T to enable centering of the cuvette T, allowing the orientation of the cuvette T to be further stabilized.

Additionally, the head portion 61 is formed such that the shape of the head portion 61 of the pressing section 60 is similar to the shape of the upper end surface of the cuvette T. This enables suppression of eccentricity resulting from pressing of the cuvette T, allowing the orientation of the cuvette T to be further stabilized.

In addition, the releasing operation performed on the cuvette T by the first cuvette conveying section 10 (or the second cuvette conveying section 11) above the cuvette disposal section 9 enables the head portion 61 subjected to the bias force of the second biasing section 63 to push the cuvette T downward. Thus, the gripping of the cuvette T by the first cuvette conveying section 10 (second cuvette conveying section 11) can be easily released.

Furthermore, based on the amount of insertion of the wedge portion 70 into the insertion part of the arm portions 51a, 51b, the wedge portion 70 enables the tilt state of the arm portions 51a, 51b to be switched between the first state where the interval between the pawl portions 52 supported by the arm portions 51a, 51b is larger than the width of the cuvette T and the second state where the interval between the pawl portions 52 supported by the arm portions 51a, 51b is substantially equal to the width of the cuvette T. Consequently, switching means for switching the tilt state of the arm portions 51a, 51b can be manufactured so as to have a simple structure, allowing manufacturability of the gripping mechanism to be improved. Furthermore, the arm portions 51a, 51b can be tiled substantially symmetrically with respect to the central axis of the cuvette T along the Y direction. Thus, for example, the orientation of the cuvette T can further be stabilized.

(Variation of the Embodiment)

The embodiment according to the present invention has been described. The specific configuration and means of the present invention may be optionally varied and improved within the scope of the technical concept of each invention recited in the claims. Such variations will be described below.

(Problems to be Solved and Effects of the Invention)

First, the problems to be solved by the invention and the effects of the invention are not limited to the above-described contents. The present invention allows problems not described above to be solved and allows effects not described above to be exerted. Furthermore, in some cases, only some of the problems are solved, and only some of the effects are exerted. For example, even if it is difficult to arrange the pressing section 60 such that, with the cuvette T held in a sandwiching manner by the sandwiching section 50, the central axis of the cuvette T in the Z direction coincides with the central axis of the pressing section 60 in the Z direction, when the arrangement of the pressing section 60 can be achieved as is the case with the related art using a technique different from the related art, the problems have been solved by the present invention.

(Gripping Object)

In the above description of the embodiment, the gripping object is a tubular container such as the cuvette T. However, the present invention is not limited to this. For example, the gripping object may be a dish-like container such as a petri dish.

(Configuration of the Support Section)

In the above description of the embodiment, the support section 40 is configured such that the longitudinal direction of the support section 40 is generally horizontal (in other words, the support section 40 is configured to lie flat) in view of safety during conveyance. However, the present invention is not limited to this. For example, the support section 40 is configured such that the longitudinal direction of the support section 40 is generally vertical (in other words, the support section 40 is configured to stand upright).

(Number of Arm Sections)

In the above description of the embodiment, the sandwiching section 50 is provided with the two arm portions 51. However, the present invention is not limited to this. For example, the sandwiching section 50 may be provided with three or more arm portions 51.

(Configuration of the Arm Sections)

In the above description of the embodiment, the arm portion 51 is provided with the first biasing section 54. However, the present invention is not limited to this. For example, the arm portions 51 may be provided with a well-known solenoid instead of the first biasing section 54.

(Number of Pawl Portions)

In the above description of the embodiment, the sandwiching section 50 is provided with the three pawl portions 52. However, the present invention is not limited to this. For example, the sandwiching section 50 may be provided with two pawl portions 52 or four or more pawl portions 52.

(First Bias Portion)

In the above description of the embodiment, the first biasing section 54 is provided between the support section 40 and the arm portion 51a (or between the support section 40 and the arm portion 51b). However, instead of the first biasing section 54, another member may be provided. Specifically, a biasing section may be provided between the upper end of the arm portion 51a and the upper end of the arm portion 51b to bias the two upper ends in a direction in which the upper ends approach each other. Alternatively, a biasing section may be provided between the pawl portion 52a and the pawl portion 52b (or the pawl portion 52c) in a direction in which the pawl portion 52a and the pawl portion 52b (or the pawl portion 52c) approach each other.

(Pressing Section)

In the above description of the embodiment, the pressing section 60 is configured to include the head portion 61, the guide section 62, and the second biasing section 63. However, the present invention is not limited to this. For example, the pressing section 60 may be configured using a well-known solenoid.

(Head Portion)

In the above description of the embodiment, the outer edge shape of the head portion 61 is set substantially similar to the outer edge shape of the upper end surface of the cuvette T. However, the head portion 61 may have another outer edge shape. For example, as long as the outer edge shape of the head portion 61 is such that the central axis of the outer edge shape of the head portion 61 coincides with the center of gravity of the outer edge shape of the upper end surface of the cuvette T, eccentricity resulting from the pressing of the cuvette T can be suppressed even when the head portion 61 does not have an outer edge shape substantially similar to the outer edge shape of the upper end surface of the cuvette T. Examples of the outer edge shape the central axis of which coincides with the center of gravity of the outer edge shape of the upper end surface of the cuvette T include polygonal planar shapes such as a general ellipse, a triangle, and a rectangle, or cross planar shapes.

Figure 9:
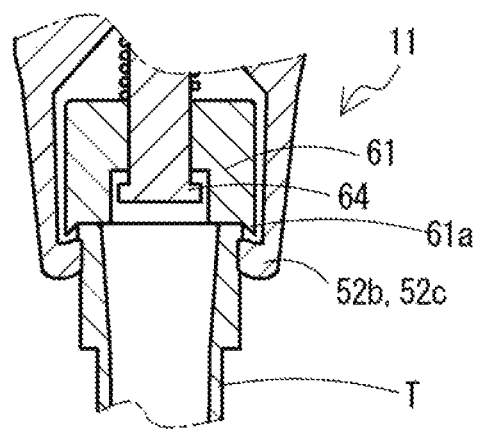
FIG. 9 is a front view depicting a variation of the gripping mechanism.

Furthermore, in the above description of the embodiment, the head portion 61 is formed using a generally cylindrical member. However, the head portion 61 may be formed so as to allow the cuvette T to be more easily and reliably centered. Specifically, as depicted in FIG. 9, the head portion 61 is formed such that an inner edge shape of the head portion 61 is smaller than the outer edge shape of the cuvette T and such that the outer edge shape of the head portion 61 is larger than the outer edge shape of the cuvette T. Furthermore, for the lower end surface of the head portion 61, a part of the lower end surface (specifically, a part of the lower end surface extending from an outer edge thereof to a point thereof opposite to an outer edge of the cuvette T) is tilted such that the outer edge 61a of the lower end surface protrudes outward and downward with respect to an inner edge of the lower end surface. Such a configuration allows the outer edge of the cuvette T to be guided along the tilt of the outer edge 61a of the head portion 61 toward the center of the head portion 61, allowing the cuvette T to be guided such that the center of the outer edge shape of the lower end surface of the head portion 61 is positioned on an extension of the central axis of the cuvette T along the Z direction. Thus, the cuvette T can be more easily and reliably centered.

(Shape of the Wedge Portion)

Figure 10A:
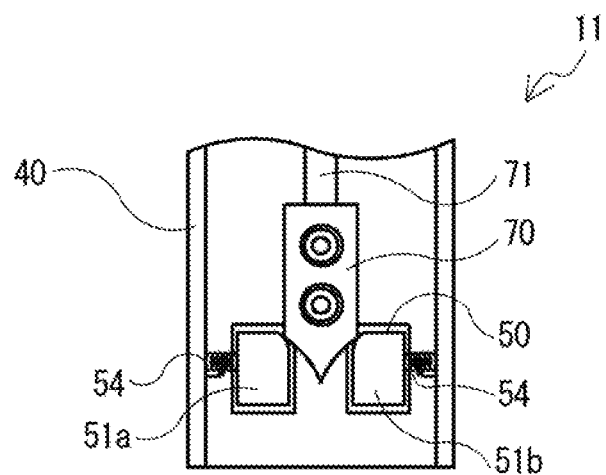
FIG. 10A shows one shape of the wedge portion of the mechanism.
Figure 10B:
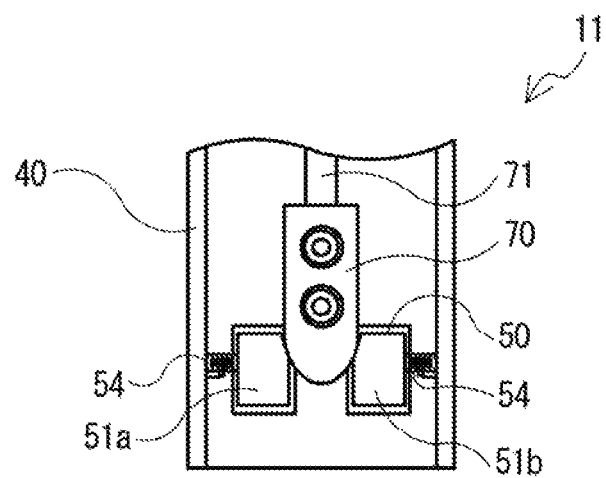
FIG. 10B shows another shape of the wedge portion of the mechanism.

In the above description of the embodiment, for the shape of the wedge portion 70, the end of the wedge portion 70 closer to the arm portions 51a, 51b is formed to have acute angles such that the interval between the upper ends of the arm portions 51a, 51b increases in proportion to the insertion amount of the wedge portion 70. However, the present invention is not limited to this. For example, the end of the wedge portion 70 may be formed to have acute angles (specifically, the end may be formed to have a tapered planar shape) such that the interval between the upper ends of the arm portions 51a, 51b increases greater rapidly than the in FIG. 6A as the insertion amount of the wedge portion 70 increases as depicted in FIG. 10A. Alternatively, the end of the wedge portion 70 may be formed to have acute angles (specifically, the end may be formed to have a generally semicircular planar shape) such that the interval between the upper ends of the arm portions 51a, 51b increases more gradually than the interval in FIG. 6A as the insertion amount of the wedge portion 70 increases as depicted in FIG. 10B. Alternatively, as the shape of the wedge portion 70, any shape may be adopted which allows the interval between the upper ends of the arm portions 51a, 51b to be changed at a desired change rate. Furthermore, in the above-described embodiment, the example has been described in which the insertion amount of the wedge portion 70 is increased in conjunction with pushing of the coupling portion 71 toward the arm portions 51a, 51b. However, the insertion amount of the wedge portion 70 may be increased in conjunction with pulling of the coupling portion 71 away from the arm portions 51a, 51b. That is, in a plane parallel to the sheets of FIGS. 6A to 8A, the wedge portion 70 may be arranged in an orientation in which the wedge portion 70 is symmetric with respect to the arm portions 51a, 51b. Then, the insertion amount of the wedge portion 70 increases as the coupling portion 71 is pulled in a direction in which the coupling portion 71 moves away from the arm portions 51a, 51b, and decreases as the coupling portion 71 is pushed in a direction in which the coupling portion 71 approaches the arm portions 51a, 51b.

(Configuration of the Wedge Driving Section)

In the above description of the embodiment, the wedge driving section 80 is configured using a well-known solenoid or the like. However, the present invention is not limited to this. For example, the wedge driving section 80 may be configured using a well-known motor (a stepping motor, a linear motor, or the like) or any other well-known driving mechanism.

In particular, when the wedge driving section 80 is configured using a well-known motor, the degree of the amount by which the wedge portion 70 protrudes may be automatically adjusted by controlling the rotation amount of the motor. Specific logic for such automatic adjustment is optional. For example, when the insertion amount of the wedge portion 70 and the mutual interval between the pawl portion 52a and the pawl portions 52b and 52c are determined not to be in the desired states based on outputs from the detection sections 90a, 90b, the desired states may be established by automatically feeding back the insertion amount of the wedge portion 70. At this time, the relative relation between the insertion amount of the wedge portion 70 and the mutual interval between the pawl portion 52a and the pawl portions 52b and 52c may vary according to the outer edge shape of the wedge portion 70 (particularly the shape of the end of the wedge portion 70 closer to the arm portions 51a, 51b). Thus, for example, change rate data used to identify such a relative relation may be pre-stored in the storage section of the measurement apparatus 1 so that the control section of the measurement apparatus 1 can control the insertion amount of the wedge portion 70 with reference to the change rate data.

The above-described conventional gripping mechanism has room for improvement in terms of the following.

For example, the mechanism in Patent Document 1 poses the following problems. When the rod portion is inserted into the upper end opening of the reaction container, friction between the rod portion and the reaction container may induce static electricity to be generated in the reaction container, with the result that the generated static electricity may cause foreign matter such as dirt or dust to be mixed into the sample in the reaction container. Furthermore, when the sample is dispensed into the reaction container, the sample may adhere to an inner upper side surface of the reaction container due to static electricity and fail to fall down to a bottom portion of the reaction container. Additionally, when the rod portion with contaminants attached thereto is inserted into the reaction container, the contaminants may be mixed into the sample in the reaction container (what is called contamination occurs). These problems may affect measurement results for the sample housed in the reaction container.

Furthermore, in the mechanism in Patent Document 2, only the recess in each grip arm of the pair of grip arms is fitted over the neck portion of the reaction container. Thus, the orientation of the reaction container gripped by the mechanism is likely to be unstable (for example, the reaction container may be tilted). Consequently, for example, when the reaction container is housed in a predetermined recess portion formed at the transfer destination location, the reaction container may have difficulty being inserted into the predetermined recess portion.

The above embodiment has been developed in view of the above-described circumstances. It is an object of the embodiment to provide a gripping mechanism that enables inhibition of possible static electricity and contamination in a gripping object such as a reaction container, while enabling the orientation of the gripping object to be stabilized.

In order to solve the above mentioned problem and achieve the above mentioned purpose, the gripping mechanism of the above mentioned embodiment is a gripping mechanism for gripping a gripping object, the gripping mechanism comprising: sandwiching means for holding the gripping object in a laterally sandwiching manner; pressing means for pressing downward an upper end surface of the gripping object held in a sandwiching manner by the sandwiching means, wherein the pressing means is arranged such that, with the gripping object being held in a sandwiching manner by the sandwiching means, a central axis of the gripping object along a vertical direction coincides mutually with a central axis of the pressing means in the vertical direction.

According to this aspect of the embodiment, the gripping mechanism comprises sandwiching means for holding the gripping object in a laterally sandwiching manner and pressing means for pressing downward an upper end surface of the gripping object held in a sandwiching manner by the sandwiching means. This prevents the sandwiching means and the pressing means from entering the inside of the gripping object, enabling suppression of possible static electricity and possible contamination in the gripping object. Furthermore, the pressing means is arranged such that, with the gripping object held in a sandwiching manner by the sandwiching means, a central axis of the gripping object along a Z direction coincides with a central axis of the pressing means along the Z direction. Thus, the orientation of the gripping object can be effectively stabilized to enable, for example, a conveying means to appropriately convey the gripping object.

Another aspect of the embodiment provides the gripping mechanism, wherein the sandwiching means comprises at least three pawl portions that are in abutting contact with the gripping object, the at least three pawl portions are arranged such that, with the gripping object being held in a sandwiching manner by the sandwiching means, a central position of a virtual circle is located on the central axis of the gripping object along the vertical direction, the virtual circle being formed substantially along a part of each of the at least three pawl portions, which is in abutting contact with the gripping object, and circumscribing the at least three pawl portions.

According to this aspect of the embodiment, pawl portions are arranged such that, with the gripping object held in a sandwiching manner by the sandwiching means, a central position of a virtual circle is located on the central axis of the gripping object along the Z direction, the virtual circle being formed substantially along a part of each of the pawl portions of the sandwiching means in abutting contact with the gripping object and circumscribing the pawl portions. Thus, the pawl portions come into abutting contact with the gripping object to enable centering of the gripping object, allowing the orientation of the gripping object to be further stabilized.

Another aspect of the embodiment provides the gripping mechanism, wherein the pressing means is formed such that a part of the pressing means that is in abutting contact with the gripping object is similar to a part of the gripping object that is in abutting contact with the pressing means.

According to this aspect of the embodiment, the pressing means is formed such that a part of the pressing means that is in abutting contact with the gripping object is similar to a part of the gripping object that is in abutting contact with the pressing means. This enables suppression of eccentricity resulting from pressing of the gripping object, allowing the orientation of the gripping object to be further stabilized.

Another aspect of the embodiment provides the gripping mechanism, which is installed on conveying means for conveying the gripping object, wherein when a receiving space is provided which is positioned below the gripping object conveyed to a part of a conveying area of the conveying means by the conveying means and gripped by the gripping mechanism, with this receiving space receiving the gripping object falling down from the gripping mechanism, an operation of canceling gripping of the gripping object by the gripping mechanism above the receiving space enables the pressing means to push the gripping object downward.

According to this aspect of the embodiment, an operation of canceling gripping of the gripping object by the gripping mechanism above the receiving space enables the pressing means to push the gripping object downward. Thus, the gripping of the gripping object by the gripping mechanism can be easily released.

Another aspect of the embodiment provides the gripping mechanism, wherein the sandwiching means comprises: a pair of rod-like arm portions provided at an interval between the arm portions, the arm portions each rotating around a rotating shaft provided in a part of the arm portion other than an end of each of the arm portions; and pawl portions each connected to an end of a corresponding arm portion of the pair of arm portions, with the end being closer to the gripping object and the pawl portions being in abutting contact with the gripping object, the gripping mechanism comprises a wedge portion that switches a tilt state of the pair of arm portions by being inserted into an insertion part between the pair of the arm portions that extends from ends of the arm portions opposite to the ends of the arm portions closer to the gripping object to the rotating shafts, and based on an amount of insertion of the wedge portion into the insertion part of the arm portions, the wedge portion enables the tilt state of the pair of the arm portions to be switched between a first state where the interval between the pawl portions connected to the pair of the arm portions is larger than a width of the gripping object and a second state where the interval between the pawl portions connected to the pair of arm portions is substantially equal to the width of the gripping object.

According to this aspect of the embodiment, based on an amount of insertion of the wedge portion into the insertion part of the arm portions, the wedge portion enables the tilt state of the pair of the arm portions to be switched between a first state where the interval between the pawl portions connected to the pair of the arm portions is larger than a width of the gripping object and a second state where the interval between the pawl portions connected to the pair of arm portions is substantially equal to the width of the gripping object. Consequently, switching means for switching the tilt state of the arm portions can be manufactured so as to have a simple structure, allowing manufacturability of the gripping mechanism to be improved. Furthermore, the arm portions can be tiled substantially symmetrically with respect to the central axis of the gripping object along the Y direction. Thus, for example, the orientation of the gripping object can further be stabilized.

EXPLANATION OF REFERENCE NUMERALS

1 Measurement apparatus
2 Housing
2a Base surface
3 Measurement mechanism
4 Cuvette supply section
5 Chip supply section
6 Reagent storage section
7 Sample storage section
8 Substrate storage section
9 Cuvette disposal section
10 First cuvette conveying section
11 Second cuvette conveying section
12 Sample conveying section
13 First reagent dispensing section
14 Second reagent dispensing section
15 Reaction tank
20 First reaction line
30 Second reaction line
31 Magnetism collecting section
32 Cleaning liquid ejecting and sucking section
33 Measurement section
40 Support section
40a Pedestal
40b, 53 Rotating shaft
41a, 41b, 42c, 43a, 55 Opening
42a, 42b Rotating shaft fixing section
43 Wedge driving section fixing section
44 Detection section fixing section
45 Bias section fixing section
50 Sandwiching section
51, 51a, 51b Arm portion
52, 52a to 52c Pawl portions
54 First biasing section
60 Pressing section
61 Head portion
61a Outer edge
62 Guide section
63 Second biasing section
64 Stopper
70 Wedge portion
71 Coupling portion
71a Projecting portion
72 Rail portion 73 Slide block
74 Third biasing section
80 Wedge driving section
90a, 90b Detection section
91 Light shielding plate
T Cuvette

What is claimed is:

1. A gripping mechanism for gripping a gripping object, the gripping mechanism comprising:
    sandwiching section configured for holding the gripping object in a laterally sandwiching manner;
    pressing section configured for pressing downward an upper end surface of the gripping object held in a sandwiching manner by the sandwiching section,
    wherein the pressing section is arranged such that, with the gripping object being held in a sandwiching manner by the sandwiching section, a central axis of the gripping object along a vertical direction coincides mutually with a central axis of the pressing section in the vertical direction,
    wherein the pressing section is further arranged such that an operation of canceling gripping of the gripping object by the gripping mechanism enables the pressing section to push the gripping object downward, and
    wherein the sandwiching section further comprises:
        a pair of rod-like arm portions provided at an interval between the arm portions, the arm portions each rotating around a rotating shaft provided in a part of the arm portion other than an end of each of the arm portions;
        one pawl portion connected to an end of a corresponding arm portion of one of the pair of arm portions, with the end being closer to the gripping object and the one pawl portion being in abutting contact with the gripping object, and
        two pawl portions each connected to an end of a corresponding arm portion of the other one of pair of arm portions, with the end being closer to the gripping object and the two pawl portions being in abutting contact with the gripping object.

2. The gripping mechanism according to claim 1, wherein the one pawl portion and the two pawl portions are arranged such that, with the gripping object being held in a sandwiching manner by the sandwiching section, a central position of a virtual circle is located on the central axis of the gripping object along the vertical direction, the virtual circle being formed substantially along a part of each of the one pawl portion and the two pawl portions, which is in abutting contact with the gripping object, and circumscribing the one pawl portion and the two pawl portions.

3. The gripping mechanism according to claim 1, wherein the pressing section is formed such that a part of the pressing section that is in abutting contact with the gripping object is similar to a part of the gripping object that is in abutting contact with the pressing section.

4. The gripping mechanism according to claim 1, wherein the gripping mechanism comprises a wedge portion that switches a tilt state of the pair of arm portions by being inserted into an insertion part between the pair of the arm portions that extends from ends of the arm portions opposite to the ends of the arm portions closer to the gripping object to the rotating shafts, and
    based on an amount of insertion of the wedge portion into the insertion part of the arm portions, the wedge portion enables the tilt state of the pair of the aim portions to be switched between a first state where the interval between the one pawl portion and the two pawl portions connected to the pair of the arm portions is larger than a width of the gripping object and a second state where the interval between the one pawl portion and the two pawl portions connected to the pair of arm portions is substantially equal to the width of the gripping object.

* * * * *